United States Patent [19]

Cannon

[11] Patent Number: 4,501,608

[45] Date of Patent: Feb. 26, 1985

[54] NITROSAMINE INHIBITION

[75] Inventor: William N. Cannon, Cumberland, Ind.

[73] Assignee: Eli Lilly and Company, Indianapolis, Ind.

[21] Appl. No.: 495,273

[22] Filed: May 16, 1983

[51] Int. Cl.³ ............................................. A01N 25/22
[52] U.S. Cl. ...................................... 71/121; 71/103; 71/DIG. 1
[58] Field of Search .................... 71/121, DIG. 1, 103

[56] References Cited

U.S. PATENT DOCUMENTS

| | | | |
|---|---|---|---|
| 4,134,917 | 1/1979 | Ross et al. | 260/577 |
| 4,226,789 | 10/1980 | Eizember et al. | 260/397.7 |
| 4,251,563 | 2/1981 | Gruetzmacher et al. | 426/605 |
| 4,331,468 | 5/1982 | Williams | 71/121 |

OTHER PUBLICATIONS

Douglass, M. L. "The Chemistry of Nitrosamine Formation, Inhibition and Destruction", J. Soc. Cosmet. Chem. 29, 581–606 (1978).

Fieser, L. F. et al. "Advanced Organic Chemistry", 1962, pp. 416–418.

Gray, J. I. et al. "Inhibition of N-Nitrosamine Formation in Model Food Systems", J. of Food Science 40, 981–984 (1975).

Mergens, W. J. et al. "Antioxidants as Blocking Agents Against Nitrosamine Formation", Autoxidation in Food & Biol. Systems, pp. 387–403 (1980).

*Primary Examiner*—Catherine L. Mills
*Attorney, Agent, or Firm*—Kathleen R. S. Page; Arthur R. Whale

[57] ABSTRACT

The present invention is directed to the inhibition of nitrosamines in dinitroaniline herbicides by the incorporation of an addition compound of an alkali metal or ammonium bisulfite with an aldehyde or ketone.

16 Claims, No Drawings

NITROSAMINE INHIBITION

BRIEF SUMMARY

Since the discovery, in the late 1970s, of the presence of nitrosamines in dinitroanilines, much effort has been directed to the removal of nitrosamines. See, e.g. U.S. Pat. Nos. 4,127,610; 4,185,035; and 4,226,789. However, it has now been discovered that the removal of nitrosamines does not necessarily eradicate all residual nitrosating species; therefore, a dinitroaniline which shows only a negligible nitrosamine content may subsequently develop a higher nitrosamine level. Circumstances which favor nitrosamine formation, notably elevated temperatures, present a special problem; yet reheating of a dinitroaniline may be necessary to achieve desired formulations. Therefore, a method is needed to stabilize dinitroanilines against subsequent nitrosamine formation.

The present invention is directed to a method of stabilizing dinitroanilines against the formation of nitrosamines, by the incorporation of an addition compound of a bisulfite with an aldehyde or ketone. The present invention is also directed to the ensuing combinations of a dinitroaniline and the addition compound of bisulfite and aldehyde or ketone.

DETAILED DESCRIPTION OF THE INVENTION

In more detail, the present invention is directed to a process for stabilizing a dinitroaniline herbicide against the formation of nitrosamines, which process comprises adding to the dinitroaniline herbicide while in molten state an effective amount of an addition comound of a bisulfite and an aldehyde or ketone.

The dinitroaniline herbicides are a well-known class of compounds. Dinitroanilines with which the present invention can be practiced (and their generic names) are
4-trifluoromethyl-2,6-dinitro-N,N-di-n-propylaniline (trifluralin);
4-isopropyl-2,6-dinitro-N,N-di-n-propylaniline (isopropalin);
4-trifluoromethyl-2,6-dinitro-N-n-butyl-N-ethylaniline (benefin);
4-trifluoromethyl-2,6-dinitro-N-ethyl-N-methallylaniline (ethalfuralin);
4-tert-butyl-2,6-dinitro-N-sec-butylaniline (butralin);
3,4-dimethyl-2,6-dinitro-N-(1-ethylpropyl)aniline (pendimethalin);
4-trifluoromethyl-2,6-dinitro-N-propyl-N-(2-chloroethyl)aniline (fluchloralin);
4-trifluoromethyl-2,6-dinitro-N-propyl-N-(cyclopropylmethyl)aniline (profluralin);
4-trifluoromethyl-2,6-dinitro-3-amino-N,N-diethylaniline (dinitramine);
4-methyl-2,6-dinitro-N,N-bis(2-chloroethyl)aniline (chlornidine);
4-sulfamoyl-2,6-dinitro-N,N-di-n-propylaniline (oryzalin);
4-(methylsulfonyl)-2,6-dinitro-N,N-di-n-propylaniline (nitralin);
N-((4-dipropylamino)-3,5-dinitrophenyl)sulfonyl)-S,S-dimethylsulfilimine (prosulfalin);
4-(trifluoromethyl)-3-amino-2,6-dinitro-N,N-di-n-propylaniline (prodiamine).

Preferred dinitroanilines with which the present invention is carried out are trifluralin, pendimethalin and fluchloralin.

Stabilization of a dinitroaniline herbicide in accordance with the present invention can be carried out with a dinitroaniline alone or with a combination of a dinitroaniline and another herbicide. As examples of other herbicides that are combined with dinitroanilines, there may be mentioned carbamates such as diallate, chlorpropham, and triallate, and triazines such as ametryn, atrazine, cyanazine, dipropetryn, metribuzin, prometon, prometryn, secbumeton, terbutryn and the like. Combinations of a dinitroaniline herbicide with a triazine which confers a higher melting temperature on the combination are especially helped by treatment in accordance with the present invention, since higher temperatures are believed to favor nitrosamine formation. Examples of such combinations are the combinations of trifluralin with either metribuzin or cyanazine.

The nitrosamine-inhibiting agent in accordance with the present invention is an addition compound of an alkali metal or ammonium bisulfite and an aldehyde or ketone. The formation of such addition compounds is well known and is described in numerous references, of which "Advanced Organic Chemistry" by Fieser and Fieser, pg. 416 et seq. (Reinhold Corp., New York, N.Y. 1962) is exemplary. The reaction proceeds as follows:

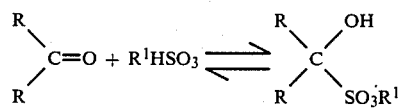

The ensuing addition products are generally crystalline salts. The scope of the reaction is dependent on the identity of the aldehyde or ketone. In general, bulkiness of the group or groups present in addition to the aldehyde or ketone function inhibits the reaction, and where the functional group is severely hindered, the reaction does not take place. Since aldehydes by definition contain hydrogen, most aldehydes will react; many methyl ketones also undergo the reaction. Higher aliphatic ketones are less likely to undergo the reaction. However, any addition compound which forms is believed to be effective for nitrosamine inhibition in accordance with the present invention.

Preferred addition compounds are those derived from an alkali metal or ammonium bisulfite and an aldehyde or ketones of the formula

wherein $R^1$ and $R^2$
(1) are taken separately and
   (a) $R^1$ represents hydrogen or methyl, and $R^2$ represents hydrogen or lower alkyl of $C_1$–$C_3$, or
   (b) $R^1$ represents hydrogen and $R^2$ represents phenyl, 2-phenylvinyl, or benzyl; or
(2) are taken together and constitute, with the carbonyl function, a cycloalkanone containing from 5 to 8 carbon atoms.

Representative aldehydes and ketones include:
formaldehyde acetaldehyde
propionaldehyde
butyraldehyde
benzaldehyde
cinnamaldehyde
phenylacetaldehyde
acetone
methyl ethyl ketone
methyl propyl ketone
methyl butyl ketone
methyl isobutyl ketone
methyl tert-butyl ketone
cyclopentanone
cyclohexanone
cyclooctanone Aldehydes and ketones which, because of cost and availability, are preferred include formaldehyde, acetaldehyde, propionaldehyde, benzaldehyde, phenylacetaldehyde, cinnamaldehyde, acetone, methyl isobutyl ketone, and cyclohexanone. Of these, the most preferred are acetone and cyclohexanone.

Suitable bisulfites in preparing the present addition compounds include sodium bisulfite, potassium bisulfite, and ammonium bisulfite. Of these, the preferred compound is sodium bisulfite.

The amount of the nitrosamine inhibitor to be employed in accordance with the present invention is not critical and will vary with such factors as the identity of the dinitroaniline, the amount, if any, of residual nitrosating species, the severity of intended subsequent conditions, and the like. In general, the present nitrosamine inhibitor is effective when present in a concentration ranging from 0.01 to 10.0 percent of the dinitroaniline, by weight. A preferred concentration is from 0.1 to 2.0 percent.

In carrying out the present invention, the present nitrosamine inhibitor is added to the dinitroaniline while in a molten state. The addition may be made as a later step in the production of the dinitroaniline; or the dinitroaniline may be subsequently remelted and the present nitrosamine inhibitor added. The former is preferred, since it confers maximum protection against nitrosamine generation. After addition of the nitrosamine inhibitor at either stage, the dinitroaniline and nitrosamine inhibitor are mixed thoroughly to insure uniform distribution of the nitrosamine inhibitor.

Dinitroaniline treated in accordance with the present invention are resistant to nitrosamine generation, even under elevated temperatures or other conditions which would normally conduce to nitrosamine formation.

The following examples illustrate the present invention and will enable those skilled in the art to practice the same. All analyses for nitrosamine were conducted on a Thermal Energy Analyzer (TEA), Model 502 TEA-GC, manufactured by Thermo-Electron Corporation, Waltham, Mass.

EXAMPLE 1: UNTREATED TRIFLURALIN, NITROSAMINE GENERATION ON HEATING

Trifluralin of a lot "A" was purified and thereafter heated. Purification was carried out as follows.

The lot A trifluralin was recrystallized from Skelly B. The resulting orange crystalline solid was then dissolved in 600 ml. of benzene and washed in sequence with five 600-ml. portions of 2N hydrochloric acid, two 600-ml. portions of water, two 600-ml. portions of 10% aqueous sodium bicarbonate solution, and two 600-ml. portions of water. The washed benzene layer was dried over anhydrous magnesium sulfate and filtered, and benzene was stripped in vacuo. The resulting trifluralin was redissolved in a small volume (about 50 ml.) of fresh benzene, and this solution was put on a Fluorisil column (wet with hexane). The trifluralin was eluted with about 4.5-5 liters of hexane, and the hexane stripped. A residual red oil crystallized on standing, and the material was recrystallized from Skelly "B".

The resulting purified trifluralin, an orange crystalline solid, was heated at 150° C. with stirring; samples were withdrawn periodically and analyzed for nitrosamine content; NDPA (nitrosodipropylamine), and $C_5$, $C_6$, $C_7$, and $C_8$ nitrosamine. Results for NDPA were as set forth in the following table.

TABLE 1

| Time | NDPA, PPM |
|---|---|
| 0 | None detected at test sensitivity of a 0.02 ppm |
| 30 min. | 0.03 |
| 1 hr. | 0.04 |
| 2 hrs. | 0.06 |
| 3 hrs. | 0.1 |
| 4 hrs. | 0.13 |
| 5 hrs. | 0.18 |
| 6 hrs. | 0.18 |

No $C_5$, $C_6$, $C_7$, and $C_8$ nitrosamine was detected in any of the samples. The 0-time sample was also analyzed for dipropylamine; none was detected (detection limit of 0.5 ppm).

EXAMPLE 2: FORMALDEHYDE SODIUM BISULFITE ADDITION COMPOUND, IN TRIFLURALIN

In a first series of tests, portions of a lot of trifluralin, lot "A", were evaluated for the increase in nitrosamine content on heating, with and without a nitrosamine inhibitor in accordance with the present invention.

A first portion of lot A was heated, with stirring, in a wax bath maintained at 110° C. Samples were withdrawn at intervals and submitted for nitrosamine analysis. Results were as follows.

TABLE II

| | Nitrosamine Found (ppm) | | | | | |
|---|---|---|---|---|---|---|
| Time | $C_5$ | $C_6$ | NDPA | $C_7$ | $C_8$ | Total |
| 0 | 0.07 | 0.15 | 0.45 | 0.39 | 0.21 | 1.27 |
| 30 min. | 0.06 | 0.14 | 0.47 | 0.38 | 0.18 | 1.23 |
| 1 hr. | 0.08 | 0.15 | 0.52 | 0.40 | 0.19 | 1.34 |
| 2 hrs. | 0.12 | 0.17 | 0.52 | 0.39 | 0.20 | 1.40 |
| 3 hrs. | 0.13 | 0.14 | 0.58 | 0.39 | 0.19 | 1.43 |
| 4 hrs. | 0.16 | 0.14 | 0.67 | 0.40 | 0.19 | 1.56 |
| 5 hrs. | 0.16 | 0.15 | 0.70 | 0.40 | 0.19 | 1.60 |
| 6 hrs. | 0.19 | 0.16 | 0.73 | 0.37 | 0.18 | 1.63 |

Another portion of lot A of trifluralin was evaluated in the same way except that the temperature was 150° C. with the following results:

TABLE III

| | Nitrosamine Found (ppm) | | | | | |
|---|---|---|---|---|---|---|
| Time | $C_5$ | $C_6$ | NDPA | $C_7$ | $C_8$ | Total |
| 0 | 0.06 | 0.19 | 0.42 | 0.37 | 0.18 | 1.22 |
| 30 min. | 0.45 | 0.18 | 1.32 | 0.42 | 0.19 | 2.56 |
| 1 hr. | 1.87 | ND* | 4.82 | 0.45 | 0.19 | 7.33 |
| 2 hrs. | 3.15 | ND | 8.37 | 0.50 | 0.19 | 12.21 |
| 3 hrs. | 3.49 | ND | 10.0 | 0.48 | 0.18 | 14.15 |
| 4 hrs. | 3.36 | ND | 10.40 | 0.45 | 0.19 | 14.40 |
| 5 hrs. | 3.40 | ND | 10.81 | 0.49 | 0.19 | 14.89 |

TABLE III-continued

| Time | Nitrosamine Found (ppm) | | | | |
|---|---|---|---|---|---|
| | $C_5$ | $C_6$ | NDPA | $C_7$ | $C_8$ | Total |
| 6 hrs. | 3.31 | ND | 10.98 | 0.49 | 0.18 | 14.96 |

*Manual attenuation of the instrument resulted in a loss of the signal for the $C_6$ nitrosamine.

A third 99-gram portion of lot A of trifluralin was melted and 1 gram of the formaldehyde sodium bisulfite addition compound (purchased from Aldrich Chemical Co.) was added. The mixture was then heated at 150° C. and samples were withdrawn at intervals and submitted for nitrosamine analysis. Results were as follows:

TABLE IV

| Time | NDPA (ppm) | Total Nitrosamines (ppm) |
|---|---|---|
| 0 | 0.54 | 1.28 |
| 30 min. | 0.65 | 1.60 |
| 1 hr. | 0.53 | 1.22 |
| 2 hrs. | 0.59 | 1.37 |
| 3 hrs. | 0.49 | 1.12 |
| 4 hrs. | 0.60 | 1.32 |
| 5 hrs. | 0.50 | 1.13 |
| 6 hrs. | 0.49 | 1.09 |

EXAMPLE 3: FORMALDEHYDE SODIUM BISULFITE ADDITION COMPOUND, DIFFERING LEVELS, IN TRIFLURALIN

Portions of a second lot of technical trifluralin, lot "B", were also evaluated for the increase in nitrosamine content on heating, with and without differing levels of formaldehyde sodium bisulfite addition compound. In this series, all portions were heated to 150° C., with stirring, and samples removed periodically and analyzed, for nitrosodipropylamine only. Results were as follows.

TABLE V

| | PPM of NDPA at Indicated Percent of Formaldehyde Sodium Bisulfite Addition Compound | | | | |
|---|---|---|---|---|---|
| Time | 0 (Control) | 1.0 | 0.5 | 0.1 | 0.05 |
| 0 | 0.4 | 0.42 | 0.33 | 0.35 | 0.34 |
| 30 min. | 2.05 | 2.02 | 1.84 | 1.49 | 1.17 |
| 1 hr. | 4.82 | 2.61 | 2.92 | 2.26 | 2.97 |
| 2 hrs. | 7.36 | 2.97 | 3.09 | 4.01 | 5.19 |
| 3 hrs. | 9.42 | 3.15 | 3.47 | 4.93 | 5.76 |
| 4 hrs. | 10.04 | 3.53 | 3.24 | 4.84 | 5.60 |
| 5 hrs. | 10.45 | 3.82 | 3.51 | 5.11 | 6.62 |
| 6 hrs. | 9.74 | 3.74 | 3.01 | 4.70 | 6.63 |

EXAMPLE 4: CYCLOHEXANONE SODIUM BISULFITE ADDITION COMPOUND, IN TRIFLURALIN

Lot B of trifluralin was employed for the evaluation of the cyclohexanone sodium bisulfite addition compound. The evaluation was carried out as reported in Example 3 except that only one level of addition compound was tested, 1.0 percent. Results were as follows:

TABLE VI

| Time | NDPA, PPM |
|---|---|
| 0 | 0.35 |
| 30 min. | 0.31 |
| 1 hr. | 0.42 |

TABLE VI-continued

| Time | NDPA, PPM |
|---|---|
| 2 hrs. | 0.44 |
| 3 hrs. | 0.55 |
| 4 hrs. | 0.52 |
| 5 hrs. | 0.82 |
| 6 hrs. | 0.88 |

EXAMPLE 5: CYCLOHEXANONE SODIUM BISULFITE ADDITION COMPOUND, DIFFERING LEVELS, IN TRIFLURALIN

Additional portions of technical trifluralin, lot B, were evaluated for the increase in nitrosamine content on heating, with and without differing levels of cyclohexanone sodium bisulfite addition compound. The evaluations were carried out as described in Example 3, with the following results:

TABLE VII

| | PPM of NDPA at Indicated Percent of Cyclohexanone Sodium Bisulfite Addition Compound | | | | |
|---|---|---|---|---|---|
| Time | 0 (Control) | 1.0 | 0.5 | 0.1 | 0.05 |
| 0 | 0.35 | 0.31 | 0.33 | 0.31 | 0.34 |
| 30 min. | 1.72 | 0.31 | 0.31 | 0.32 | 0.39 |
| 1 hr. | 4.22 | 0.37 | 0.37 | 0.48 | 0.68 |
| 2 hrs. | 7.30 | 0.33 | 0.72 | 0.53 | 0.79 |
| 3 hrs. | 9.04 | 0.41 | 0.87 | 0.57 | 1.04 |
| 4 hrs. | 9.79 | 0.41 | 1.06 | 0.90 | 1.64 |
| 5 hrs. | 10.51 | 0.48 | 1.24 | 1.59 | 3.83 |
| 6 hrs. | 10.84 | 0.51 | 1.26 | 1.95 | 4.85 |

EXAMPLE 6: ACETONE SODIUM BISULFITE ADDITION COMPOUND, DIFFERING LEVELS, IN TRIFLURALIN

Additional portions of technical trifluralin, lot B, were evaluated for the increase in nitrosamine content on heating, with and without differing levels of acetone sodium bisulfite addition compound. The evaluations were carried out as described in Example 3, with the following results.

TABLE VIII

| | PPM of NDPA at Indicated Percent of Acetone Sodium Bisulfite Addition Compound | | | | |
|---|---|---|---|---|---|
| Time | 0 (Control) | 1.0 | 0.5 | 0.1 | 0.05 |
| 0 | 0.34 | 0.33 | 0.33 | 0.32 | 0.37 |
| 30 min. | 2.06 | 0.36 | 0.37 | 0.65 | 1.43 |
| 1 hr. | 4.35 | 0.38 | 0.51 | 0.99 | 1.88 |
| 2 hrs. | 7.13 | 0.35 | 0.63 | 1.25 | 2.12 |
| 3 hrs. | 8.71 | 0.38 | 0.86 | 1.65 | 3.00 |
| 4 hrs. | 9.72 | 0.41 | 0.97 | 2.21 | 4.05 |
| 5 hrs. | 10.65 | 0.41 | 1.05 | 2.92 | 4.50 |
| 6 hrs. | 11.15 | 0.40 | 1.03 | 3.65 | 6.50 |

EXAMPLES 7-12: SODIUM BISULFITE ADDITION COMPOUNDS OF VARIOUS ALDEHYDES AND KETONES, IN TRIFLURALIN

Various sodium bisulfite addition compounds were evaluated for their inhibition of nitrosamine formation upon heating of technical trifluralin, lot B. The procedures were those described in Example 3, except that only a single level was evaluated. Results were as described in the following table.

TABLE IX

PPM of NDPA Employing 1 Percent of Addition Compound of Sodium Bisulfite and Indicated Aldehyde or Ketone

| Time | Control | Methyl Ethyl Ketone | Benzal-dehyde | Cinnamal-dehyde | Propional-dehyde | Methyl Isobutyl Ketone | Phenyl-Acetaldehyde |
|---|---|---|---|---|---|---|---|
| 0 | 0.36 | 0.43 | 0.37 | 0.35 | 0.34 | 0.37 | 0.31 |
| 30 min. | 1.63 | 0.34 | 1.01 | 0.99 | 0.59 | 0.93 | 0.34 |
| 1 hr. | 3.28 | 0.43 | 1.01 | 0.68 | 1.40 | 1.13 | 0.26 |
| 2 hrs. | 4.49 | 0.55 | 0.71 | 0.77 | 1.09 | 1.04 | 0.33 |
| 3 hrs. | 4.53 | 0.56 | 0.87 | 0.93 | 1.17 | 1.02 | 0.28 |
| 4 hrs. | 4.16 | 0.45 | 0.84 | 0.86 | 1.17 | 0.94 | 0.24 |
| 5 hrs. | 4.20 | 0.44 | 0.96 | 1.01 | 1.40 | 1.00 | 0.23 |
| 6 hrs. | 3.70 | 0.48 | 0.96 | 1.14 | 1.54 | 0.97 | 0.20 |

EXAMPLES 13-14: METHYL ETHYL KETONE ADDITION COMPOUNDS OF VARIOUS BISULFITES, IN TRIFLURALIN

Addition compounds of methyl ethyl ketone with potassium and ammonium bisulfite were evaluated for their inhibition of nitrosamine formation upon heating of technical trifluralin, lot B. The procedures were those described in Example 3, except that only a single level was evaluated. Results were as described in the following table.

TABLE X

PPM of NDPA Employing 1 Percent of Indicated Addition Compound

| Time | Control | Addition Compound With Potassium Bisulfite | Addition Compound With Ammonium Bisulfite |
|---|---|---|---|
| 0 | 0.26 | 0.35 | 0.28 |
| 30 min. | 1.34 | 0.51 | 0.68 |
| 1 hr. | 2.08 | 0.82 | 1.39 |
| 2 hrs. | 3.64 | 0.84 | 2.19 |
| 3 hrs. | 3.68 | 0.97 | 1.93 |
| 4 hrs. | 4.58 | 1.03 | 2.04 |
| 5 hrs. | 4.11 | 0.97 | 2.47 |
| 6 hrs. | 3.49 | 0.92 | 2.33 |

EXAMPLE 15: METHYL ETHYL KETONE SODIUM BISULFITE ADDITION COMPOUND, IN BENEFIN

A mixture of 99 grams of benefin and 1 gram of methyl ethyl ketone sodium bisulfite addition compound was heated at 150° C. Samples were withdrawn at intervals and analyzed for butylethylnitrosamine (BENA).

A sample of the same lot of benefin was heated without any additive. Samples were also withdrawn at the same intervals and analyzed for BENA, C-5 and C-6 nitrosamines, and total nitrosamine content. Results were as set forth in the following table.

TABLE XI

PPM of Indicated Nitrosamine

| | No Additive (Control) | | | | 1 Percent of Methyl Ethyl Ketone Sodium Bisulfite Addition Compound |
|---|---|---|---|---|---|
| Time | BENA | C-5 | C-6 | Total | BENA |
| 0 | 0.11 | — | — | 0.11 | 0.07 |
| 30 min. | 0.15 | — | 0.09 | 0.24 | 0.3 |
| 1 hr. | 0.71 | 0.15 | 0.47 | 1.33 | 0.28 |
| 2 hrs. | 1.1 | 0.11 | 0.43 | 1.64 | 0.26 |
| 3 hrs. | 1.64 | 0.14 | 0.54 | 2.32 | 0.38 |
| 4 hrs. | 2.51 | 0.24 | 0.67 | 3.42 | 0.43 |
| 5 hrs. | 2.86 | 0.24 | 0.68 | 3.78 | 0.46 |
| 6 hrs. | 3.01 | 0.20 | 0.59 | 3.80 | 0.34 |

EXAMPLE 16: METHYL ETHYL KETONE SODIUM BISULFITE ADDITION COMPOUND, IN ETHALFLURALIN

The procedures of Example 15 were repeated with ethalfluralin instead of benefin, and with analysis for ethylmethallylnitrosamine (EMANA) and, in the case of control, C-8 nitrosamines and total nitrosamines. Results were as set forth in the following table.

TABLE XII

PPM of Indicated Nitrosamine

| | No Additive (Control) | | | 1 percent of Methyl Ethyl Ketone Sodium Bisulfite Addition Compound |
|---|---|---|---|---|
| Time | EMANA | C-8 | Total | EMANA |
| 0 | 0.63 | 0.11 | 0.74 | 1.22 |
| 30 min. | 4.64 | 0.52 | 5.16 | 7.34 |
| 1 hr. | 18.2 | 2.89 | 21.09 | 2.56 |
| 2 hrs. | 24.5 | 2.99 | 27.49 | 6.39 |
| 3 hrs. | 24.4 | 3.87 | 28.27 | 7.64 |
| 4 hrs. | 23.1 | 3.10 | 26.2 | 7.19 |
| 5 hrs. | 19.3 | 3.57 | 22.87 | 6.92 |
| 6 hrs. | 21.6 | 3.04 | 24.64 | 6.55 |

EXAMPLE 17: ACETONE SODIUM BISULFITE ADDITION COMPOUND, IN TRIFLURALIN

Crystalline acetone sodium bisulfite addition compound (3 grams) was added to molten technical trifluralin, lot B (297 grams), providing a 1 percent concentration of the addition compound. The mixture was stirred slowly and heated in a wax bath maintained at 70° C. Samples were withdrawn at intervals and analyzed for NDPA content. A control was also run. Results were as follows:

TABLE XIII

PPM of NDPA

| Time | No Additive (Control) | 1 Percent Acetone Sodium Bisulfite Addition Compound |
|---|---|---|
| 0 | 0.50 | 0.55 |
| 1 hr. | 0.46 | 0.54 |
| 2 hrs. | 0.39 | 0.49 |
| 4 hrs. | 0.45 | 0.51 |
| 8 hrs. | 0.49 | 0.53 |
| 24 hrs. | 0.45 | 0.54 |

TABLE XIII-continued

| | PPM of NDPA | |
|---|---|---|
| Time | No Additive (Control) | 1 Percent Acetone Sodium Bisulfite Addition Compound |
| 48 hrs. | 0.32 | 0.51 |
| 72 hrs. | 0.46 | 0.50 |

Although these data indicate little nitrosamine formation, they should be compared with Example 2. It is believed that nitrosamine formation is accelerated with increasing temperatures, and that 70° C. does not enhance nitrosamine formation much beyond ambient temperatures.

EXAMPLES 18-19

Evaluations of two of the present nitrosamine inhibitors, acetone sodium bisulfite addition compound and cyclohexanone sodium bisulfite addition compound, were repeated. Trifluralin of a lot "C" was employed in these evaluations. Portions of the trifluralin, alone or with one of the additives, were heated to 110° C.; samples were withdrawn periodically and analyzed for NDPA. Results were as shown in the following tables.

A first evaluation compared acetone sodium bisulfite addition compound with cyclohexanone sodium bisulfite addition compound at equivalent mole percents.

TABLE XIV

| | PPM of NDPA With Indicaied Addition Compound | | | |
|---|---|---|---|---|
| Time (Hours) | Control | 1.0 Percent by Weight (2 mole percent) of Acetone Sodium Bisulfite Addition Compound | | 1.2 Percent by Weight (2.0 mole percent) of Cyclohexanone Sodium Bisulfite Addition Compound |
| 0 | 1.0 | 0.80 | 0.95 | 0.87 | 0.97 |
| 3 | 0.9 | 0.92 | 1.0 | 0.59 | 0.81 |
| 19 | 2.6 | 1.3 | 1.1 | 0.94 | 1.0 |
| 27 | 3.6 | 1.1 | 1.0 | 1.1 | 1.0 |
| 43 | 4.7 | 1.3 | 1.3 | 1.1 | 0.79 |

A second evaluation repeated the comparison, but with two different levels.

TABLE XV

| | PPM of NDPA With Indicated Addition Compound | | | | |
|---|---|---|---|---|---|
| | | Acetone Sodium Bisulfite Addition Compound | | Cyclohexanone Sodium Bisulfite Addition Compound | |
| Time (Hours) | Control | 0.05 percent by Weight (0.1 mole percent) | 5.0 percent by Weight (10.0 mole percent) | 0.06 percent by Weight (0.1 mole percent) | 6.0 percent by Weight (10.0 mole percent) |
| 0 | 0.99 | 0.89 | 1.0 | 1.0 | 0.72 |
| 3 | 1.2 | 0.85 | 1.1 | 1.2 | 0.71 |
| 20 | 1.2 | 1.2 | 1.2 | 1.3 | 0.29 |
| 27 | 2.6 | 1.2 | 1.1 | 2.0 | 0.67 |
| 43 | 3.4 | 1.2 | 0.56 | 2.6 | 0.35 |

A third evaluation again compared the two addition compounds, at two different levels, and with two different sources of one of the addition compounds.

TABLE XVI

| | PPM of NDPA With Indicated Addition Compound | | | | | |
|---|---|---|---|---|---|---|
| | | Acetone Sodium Bisulfite Addition Compound, Non-Commercial Source | Acetone Sodium Bisulfite Addition Compound, Commercial Source | | Cyclohexanone Sodium Bisulfite Addition Compound | |
| Time (Hours) | Control | 0.05 Percent By Weight (0.1 mole Percent) | 0.05 Percent by Weight (0.1 mole Percent) | 1.0 Percent by Weight (2.0 mole Percent) | 0.06 Percent by Weight (0.1 mole Percent) | 1.2 Percent by Weight (2.0 mole Percent) |
| 0 | 0.48 | 0.55 | 0.58 | 0.52 | 0.42 | 0.47 |
| 7 | 1.6 | 1.3 | 0.42 | 0.52 | 0.24 | 0.58 |
| 23 | 1.5 | 1.3 | 0.96 | 0.47 | 0.83 | 0.15 |
| 31 | 4.3 | 1.8 | 1.7 | 0.60 | 0.66 | 0.49 |
| 48 | 5.2 | 8.0 | 3.8 | 0.62 | 1.7 | 0.40 |
| 48* | 6.1 | 5.6 | 4.3 | 0.53 | 2.0 | 0.44 |

*Reassay of sample.

EXAMPLE 20: PREPARATION OF ACETONE SODIUM BISULFITE ADDITION COMPOUND

Reagent grade acetone (58 grams; 1.0 mole) was added slowly to a saturated aqueous sodium bisulfite solution (200 ml.). The reaction mixture became warm during the addition, and after the addition of about half of the acetone, a crystalline precipitate began to form. After addition of the acetone was complete, the reaction mixture was stirred for a few minutes, stoppered and allowed to cool to room temperature. The reaction mixture was maintained at room temperature overnight (about 18 hours), then 200 ml. of ethanol was added, the solid material broken up, then collected by suction filtration. The solid material was washed on the filter with two 100-ml. portions of cold ethanol, then with diethyl ether and air dried at room temperature. The resulting material was a white crystalline solid. The identity of the product was confirmed by NMR; the NMR spectrum was in agreement with the spectrum given in the Sadtler NMR collection for the same compound, spectrum 16891M.

I claim:

1. A process for stabilizing a dinitroaniline herbicide against formation of nitrosamines, said dinitroaniline herbicide being selected from the group consisting of
trifluralin,
isopropalin,
benefin,
ethalfluralin,
butralin,
pendimethalin,
fluchloralin,
profluralin,
dinitramine,
chlornidine,
oryzalin,
nitralin,
prosulfalin, and
prodiamine
which process comprises adding to the dinitroaniline herbicide, while in a molten state, an effective amount of an addition compound of an alkali metal or ammonium bisulfite and an aldehyde or ketone of the formula

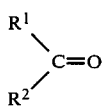

wherein $R^1$ and $R^2$
(1) are taken separately and
(a) $R^1$ represents hydrogen or methyl, and $R^2$ represents hydrogen or lower alkyl of $C_1$-$C_3$, or
(b) $R^1$ represents hydrogen and $R^2$ represents phenyl, 2-phenylvinyl, or benzyl; or
(2) are taken together and constitute, with the carbonyl function, a cycloalkanone containing from 5 to 8 carbon atoms.

2. The process of claim 1 wherein the aldehyde or ketone is cyclohexanone.

3. The process of claim 1 wherein the aldehyde or ketone is acetone.

4. The process of claim 3 wherein the dinitroaniline herbicide is trifluralin.

5. The process of claim 3 wherein the dinitroaniline herbicide is benefin.

6. The process of claim 3 wherein the dinitroaniline herbicide is ethalfluralin.

7. The process of claim 3 wherein the dinitroaniline herbicide is pendimethalin.

8. The process of claim 3 wherein the dinitroaniline herbicide is fluchloralin.

9. A composition produced by the process of claim 1.

10. The composition of claim 9 wherein the aldehyde or ketone is cyclohexanone.

11. The composition of claim 9 wherein the aldehyde or ketone is acetone.

12. The composition of claim 11 wherein the dinitroaniline herbicide is trifluralin.

13. The composition of claim 11 wherein the dinitroaniline herbicide is benefin.

14. The composition of claim 11 wherein the dinitroaniline herbicide is ethalfluralin.

15. The composition of claim 11 wherein the dinitroaniline herbicide is pendimethalin.

16. The composition of claim 11 wherein the dinitroaniline herbicide is fluchloralin.

* * * * *

UNITED STATES PATENT AND TRADEMARK OFFICE
CERTIFICATE OF CORRECTION

PATENT NO.   : 4,501,608
DATED        : February 26, 1985
INVENTOR(S)  : Willian N. Cannon It is certified that error appears in the above—identified patent and that said Letters Patent is hereby corrected as shown below:

On the title page under References Cited:
  Add the following U.S. Patent:
    4,335,260  6/1982  Bornengo et al.........564/406,407
  Add the following after U.S. Patent Documents and before Other Publications:
    FOREIGN PATENT DOCUMENTS
        92,591  2/1983  EPO
     1,549,225  7/1979  United Kingdom Column 1, line 48, "ethalfuralin" should read --ethalfluralin--.

Column 4, about line 28, "and" should read --or--.

Column 9, about line 61, "Indicaied" should read --Indicated--.

Column 10, line 2, "Indicaied" should read --Indicated--.

Signed and Sealed this

Eighteenth Day of November, 1986

Attest:

DONALD J. QUIGG

Attesting Officer

Commissioner of Patents and Trademarks